United States Patent [19]

Yokoi et al.

[11] Patent Number: 5,585,511
[45] Date of Patent: Dec. 17, 1996

[54] PLATINUM COMPLEX AND MALIGNANT TUMOR TREATING DRUG CONTAINING THE SAME

[75] Inventors: Koichi Yokoi; Kinichi Mogi; Hidehiko Kohya; Mari Ohtsuka; Hiroyuki Mizuno; Susumu Sato; Tadayuki Kuraishi, all of Chiba, Japan

[73] Assignee: SS Pharmaceutical Co., Ltd., Tokyo, Japan

[21] Appl. No.: 578,490

[22] Filed: Dec. 26, 1995

[30] Foreign Application Priority Data

Dec. 26, 1994 [JP] Japan .................................. 6-322542

[51] Int. Cl.$^6$ ............................ C07F 15/00; A61K 31/28
[52] U.S. Cl. ............................................ 556/137; 514/492
[58] Field of Search ............................ 556/137; 502/492

[56] References Cited

U.S. PATENT DOCUMENTS

| 4,560,781 | 12/1985 | Totani et al. | 556/137 |
| 4,968,826 | 11/1990 | Totani et al. | 556/137 |

FOREIGN PATENT DOCUMENTS

| 98121 | 1/1984 | European Pat. Off. . |
| 127884 | 12/1984 | European Pat. Off. . |
| 136012 | 4/1985 | European Pat. Off. . |
| 0212497 | 8/1990 | Japan . |

OTHER PUBLICATIONS

*Chemical Abstracts*, vol. 110, No. 15, Apr. 10, 1989, p. 30, abstract No. 128,160j.
*Chemical Abstracts*, vol. 99, No. 25, Dec. 19, 1983, p. 31, abstract No. 205,716d.

*Primary Examiner*—Porfirio Nazario-Gonzalez
*Attorney, Agent, or Firm*—Sughrue, Mion, Zinn, Macpeak & Seas

[57] ABSTRACT

A platinum complex represented by the following formula (1):

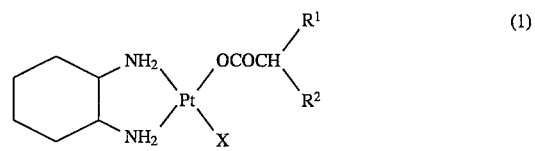

wherein the all symbols are defined in the disclosure; and a malignant tumor treating drug which contains the complex as an active ingredient. The platinum complex is excellent in antitumor effects and safety and is highly soluble in water, and therefore it is useful as an agent for use in the treatment of various malignant tumors.

7 Claims, No Drawings

PLATINUM COMPLEX AND MALIGNANT TUMOR TREATING DRUG CONTAINING THE SAME

FIELD OF THE INVENTION

This invention relates to a novel platinum complex having excellent antitumor effect and high safety and a malignant tumor treating drug which contains the platinum complex.

BACKGROUND OF THE INVENTION

Various antitumor substances have been developed for use in the treatment of malignant tumors which are now the most highest cause of death. Among these substances, an antitumor platinum compound, cisplatin, has a broad range of antitumor spectrum and takes an important role in the chemotherapy of various tumors. However, cisplatin has a problem of causing side effects such as renal toxicity, blood toxicity, digestive organ toxicity, nervous toxicity and the like. In consequence, attempts have been made to develop antitumor agents which have low toxicity and high antitumor effects.

For example, it has been reported that a compound in which platinum is coordinated to 1,2-diaminocyclohexane has excellent antitumor effect and relatively high safety (JP-A-2-212497, JP-B-3-66318 and JP-B-4-79353; the terms "JP-A" and "JP-B" as used herein respectively means an "unexamined published Japanese patent application" and an "examined Japanese patent publication").

These antitumor substances, however, have disadvantages in that their pharmacological effects and safety are not always satisfactory and their administration by injection are limited because of their low solubility in water.

SUMMARY OF THE INVENTION

In consequence, it therefore becomes an object of the present invention to provide a platinum complex which has excellent antitumor effects, high safety and good water solubility and a malignant tumor treating drug that contains the platinum complex.

In view of the above, the inventors of the present invention have conducted intensive studies and found that a platinum complex represented by the following formula (1) shows excellent antitumor effects, high safety and good water solubility. The present invention has been accomplished on the basis of this finding.

Thus, according to the present invention, there is provided a platinum complex represented by the following formula (1):

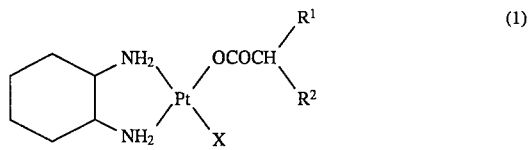

wherein X represents a halogen atom or a nitrate ion, and $R^1$ and $R^2$ may be the same or different from each other and each represents a hydrogen atom, a halogen atom, a hydroxyl group or an alkyl group, or both form a cycloalkyl group together with the adjacent carbon atom.

The present invention also provides a drug for use in the treatment of malignant tumors, which contains the platinum complex represented by the above formula (1) as an active ingredient.

Other objects and advantages of the present invention will be made apparent as the description progresses.

DETAILED DESCRIPTION OF THE INVENTION

In the platinum complex of the present invention represented by the aforementioned formula (1), preferred examples of the alkyl group of $R^1$ and $R^2$ include straight-chain or branched- alkyl groups having 1 to 9 carbon atoms, more preferably straight-chain or branched- alkyl groups having 1 to 6 carbon atoms. Specific examples of the groups include methyl, ethyl, n-propyl, isopropyl, n-butyl, isobutyl, sec-butyl, tert-butyl, n-pentyl, n-hexyl, n-heptyl, n-octyl, n-nonyl and the like groups, of which methyl, ethyl, n-propyl, isopropyl, n-butyl, n-pentyl and n-hexyl are particularly preferred. Specific examples of the halogen atom represented by $R^1$ and $R^2$ include fluorine, chlorine, bromine and iodine. Specific examples of the cycloalkyl group which is formed by $R^1$ and $R^2$ together with the adjacent carbon atom include 3- to 7-membered cycloalkyl groups such as cyclopropyl, cyclobutyl, cyclopentyl, cyclohexyl, cycloheptyl and the like groups. Specific examples of the halogen atom represented by X in the formula (1) include fluorine, chlorine, bromine and iodine.

Cis-, trans-1-, trans-d- or the like stereoisomerism is present in the 1,2-diaminocyclohexane moiety of formula (1), and the platinum complex of the present invention may be any one of these isomers or a mixture thereof. Hydrate and the like solvates are also included in the platinum complex of the present invention.

Among the platinum comples (1) of the present invention, Compounds 3, 10, 14, 17, which will be described below, are particularly preferred, though the present invention is not limited to these specific examples.

The platinum complex (1) of the present invention can be produced in accordance, for example, with the following reaction scheme.

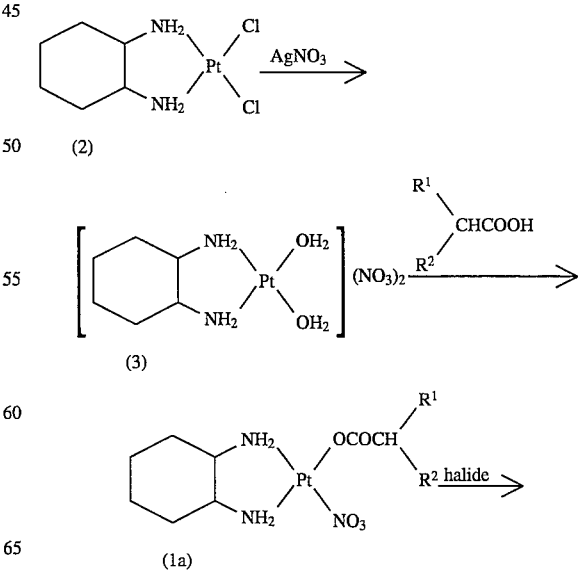

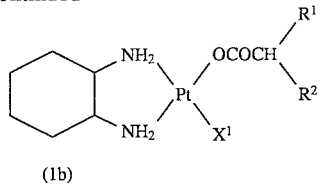

(1b)

(In the above formulae, $X^1$ represents a halogen atom, and $R^1$ and $R^2$ are as defined in the foregoing.)

That is, a compound (1a) can be obtained by allowing a platinum compound (2) to react with silver nitrate to form a diaquo complex (3) and then allowing the complex to react with a carboxylic acid represented by $R^1R^2CHCOOH$ or a salt thereof, and a compound (1b) can be obtained by allowing the compound (1a) to react with a halide such as potassium chloride. These compounds (1a) and (1b) are the intended platinum complex (1) of the present invention.

More particularly, it is preferred to produce the platinum complex of the present invention in the following manner.

Firstly, the compound (2) is suspended in water and mixed with silver nitrate, and the mixture is stirred for generally 1 to 8 hours to effect the reaction. In this case, silver nitrate is used preferably in an amount of 1.8 to 2 moles per 1 mole of the compound (2). The reaction may be carried out at a temperature of preferably from 0° to 60° C., more preferably from 0° to 40° C. After completion of the reaction, the thus formed precipitate of silver iodide is removed by filtration to obtain an aqueous solution of the diaquo complex (3).

Thereafter, the compound (1a) is obtained by allowing the thus obtained diaquo complex aqueous solution to react with a carboxylic acid $R^1R^2CHCOOH$ and an alkali aqueous solution. In this reaction, it is preferred to use the carboxylic acid in an amount of from 1 to 5 moles, more preferably from 1 to 2 moles, and the alkali in an amount of from 0.4 to 1 mole, per 1 mole of the diaquo complex, and the reaction may be carried out at a temperature of preferably from 0° to 60° C., more preferably from 10° to 40° C., for a period of from 1 hour to 1 day. After completion of the reaction, the reaction solution is allowed to stand at 0° C. to room temperature as such or after it is concentrated to obtain crystals of the compound (1a). In this instance, the alkali to be used is preferably sodium hydroxide, potassium hydroxide or the like.

The compound (1b) is obtained when the thus obtained compound (1a) is suspended in water or formamide and stirred in the presence of a halide such as potassium chloride, potassium bromide or the like. This reaction may be carried out at a temperature of preferably from 10° to 40° C.

The thus obtained platinum complex (1) of the present invention is useful as a malignant tumor treating drug, because it shows excellent antitumor effect, causes less side effects and has high solubility in water.

When the platinum complex (1) is administered to mammals including human as a malignant tumor treating agent, it is preferred, in general, to make the complex into a pharmaceutical composition by combining it with a pharmaceutically acceptable carrier. Specific examples of the pharmaceutical composition include a composition for use in intravenous injection, intramuscular injection, tumor injection or the like, a composition for oral administration use, a composition for rectal administration use and the like, of which the composition for injection use is particularly preferred. Specific examples of the pharmaceutically acceptable carrier to be used herein include distilled water for injection use, physiological saline, a buffer solution and the like.

The dose of the malignant tumor treating drug of the present invention varies depending on the conditions, age, body weight and the like of each patient. In the case of injection, the dose may be preferably from 3 mg/m$^2$ to 150 mg/m$^2$ per day as the platinum complex (1), and the daily dose may be divided into 1 to 3 doses per day.

The following examples are provided to further illustrate the present invention. It is to be understood, however, that the examples are for purpose of illustration only and are not intended as a definition of the limits of the invention.

EXAMPLE 1

(Compound 1)

A 5.70 g (15 mmol) portion of dichloro(trans-1-1,2-diaminocyclohexane)platinum(II) was suspended in 150 ml of water, and 5.10 g (30 mmol) of silver nitrate was added to the suspension, followed by stirring the resulting mixture at room temperature for 5 hours. After completion of the reaction, the thus precipitated silver chloride was removed by filtration. The thus obtained filtrate was concentrated to about 100 ml to which were subsequently added 1.80 g (30 mmol) of acetic acid and then 14 ml of a 1N aqueous solution of sodium hydroxide while stirring.

The reaction solution was allowed to stand at room temperature for 3 days, and the thus precipitated crystals were collected by filtration, washed with water and then dried to obtain 4.35 g (66.1%) of crystals of acetato(nitrato)(trans-1-1,2-diaminocyclohexane)platinum(ii) ($C_8H_{17}N_3O_5Pt \cdot \frac{1}{2}H_2O$).

Melting point: 220°–225° C. (decomposition) Elemental analysis data: calcd. (%): C, 21.87; H, 4.13; N, 9.56 found (%): C, 21.67; H, 4.42; N, 9.63 $^{195}$Pt NMR (DMF-d$_7$) δ: −1649 $^1$H NMR (DMF-d$_7$) δ: 1.19 (2H, m), 1.55 (4H, m), 1.96 (3H, s), 2.12 (2H, m), 2.64 (2H, m), 5.80 (1H, br m), 6.11 (1H, br m), 6.83 (1H, br m), 6.95 (1H, br m)

EXAMPLE 2

(Compound 2)

The procedure of Example 1 was repeated except that dichloro(trans-dl-1,2-diaminocyclohexane)Platinum(II) was used instead of dichloro(trans-1-1,2-diaminocyclohexane)platinum(II), thereby obtaining 4.87 g of crystals of acetato(nitrato)(trans-dl-1,2-diaminocyclohexane)platinum(II) ($C_8H_{17}N_3O_5Pt \cdot \frac{1}{2}H_2O$).

Melting point: 220°–225° C. (decomposition) Elemental analysis data: calcd. (%): C, 21.87; H, 4.13; N, 9.56 found (%): C, 21.82; H, 4.03; N, 9.72 $^{195}$Pt NMR (DMF-d$_7$) δ: −1649 $^1$H NMR (DMF-d$_7$) δ: 1.19 (2H, m), 1.55 (4H, m), 1.96 (3H, s), 2.12 (2H, m), 2.64 (2H, m) , 5.80 (1H, br m), 6.11 (1H, br m) , 6.83 (1H, br m), 6.95 (1H, br m)

EXAMPLE 3

(Compound 3)

The procedure of Example 1 was repeated except that 2.28 g (30 mmol) of glycolic acid was used instead of acetic acid and the amount of the 1 N aqueous solution of sodium hydroxide was changed to 7 ml, thereby obtaining glycolate(nitrato)(trans-1-1,2-diaminocyclohexane)platinum(II) ($C_8H17N_3O_6Pt$).

Melting point: 225°–230° C. (decomposition) Elemental analysis data: calcd. (%): C, 21.53; H, 3.84; N, 9.41 found (%): C, 21.44; H, 3.73; N, 9.37 $^{195}$Pt NMR (DMF-d$_7$) δ:

−1645 $^1$H NMR (DMF-dT) δ: 1.20 (2H, m), 1.55 (4H, m), 2.13 (2H, m), 2.67 (2H, m), 4.06 (2H, s), 5.42 (1H, br), 5.81 (1H, br m), 6.21 (1H, br m), 6.94 (2H, br m)

EXAMPLE 4

(Compound 4)

The procedure of Example 3 was repeated except that dichloro(trans-dl-1,2-diaminocyclohexane)platinum(II) was used instead of dichloro(trans-1-1,2-diaminocyclohexane) platinum(II), thereby obtaining 3.85 g (57.5%) of crystals of glycolato(nitrato)(trans-dl-1,2-diaminocyclohexane)platinum(II) ($C_8H_{17}N_3O_6Pt$).

Melting point: 225°–230° C. (decomposition) Elemental analysis data: calcd. (%): C, 21.53; H, 3.84; N, 9.41 found (%): C, 21.73; H, 3.83; N, 9.42 $^{195}$Pt NMR (DMF-$d_7$) δ: −1645 $^1$H NMR (DMF-$d_7$) δ: 1.20 (2H, m), 1.55 (4H, m), 2.13 (2H, m), 2.67 (2H, m), 4.06 (2H, s), 5.42 (1H, br), 5.81 (1H, br m), 6.21 (1H, br m), 6.94 (2H, br m)

EXAMPLE 5

(Compound 5)

The procedure of Example 1 was repeated except that 2.22 g (30 mmol) of propionic acid was used instead of acetic acid and the amount of the 1 N aqueous solution of sodium hydroxide was changed to 13 ml, thereby obtaining 4.75 g (71.3%) of crystals of propionato(nitrato)(trans-1-1, 2diaminocyclohexane)platinum(II) ($C_9H_{19}N_3O_5Pt$).

Melting point: 225°–233° C. (decomposition) Elemental analysis data: calcd. (%): C, 24.33; 4.31; N, 9.46 found (%): C, 24.54; H, 4.21; N, 9.42 $^{195}$Pt NMR (DMF-$d_7$) δ: −1651 $^1$H NMR (DMF-$d_7$) δ: 0.92 (3H, t, $J_{H-H}$=7.2 Hz), 1.19 (2H, m), 1.56 (4H, m), 2.13 (2H, m), 2.25 (2H, q, $J_{H-H}$=7.2 Hz), 2.65 (2H, m), 5.83 (1H, br m), 6.12 (1H, br m), 6.83 (1H, br m), 6.98 (1H, br m)

EXAMPLE 6

(Compound 6)

The procedure of Example 1 was repeated except that 2.58 g (30 mmol) of cyclopropanecarboxylic acid was used instead of acetic acid and the amount of the 1 N aqueous solution of sodium hydroxide was changed to 12 ml, thereby obtaining 4.99 g (73.0%) of crystals of cyclopropanecarboxylato (nitrato) (trans-1-1,2-diaminocyclohexane) platinum (II) ($C_{10}H_{19}N_3O_5Pt$).

Melting point: 218°–221° C. (decomposition) Elemental analysis data: calcd. (%): C, 26.32; H, 4.20; N, 9.21 found (%): C, 26.02; H, 4.15; N, 9.28 $^{195}$Pt NMR (DMF-$d_7$) δ: −1633 $^1$H NMR (DMF-$d_7$) δ: 0.77 (4H, m), 1.19 (2H, m), 1.53 (5H, m), 2.12 (2H, m), 2.64 (2H, m), 5.72 (1H, br m), 6.07 (1H, br m), 6.80 (1H, br m), 6.90 (1H, br m)

EXAMPLE 7

(Compound 7)

The procedure of Example 1 was repeated except that 3.42 g (30 mmol) of cyclopentanecarboxylic acid was used instead of acetic acid and the amount of the 1 N aqueous solution of sodium hydroxide was changed to 10 ml, thereby obtaining 4.01 g (55.3%) of crystals of cyclopentane-carboxylato(nitrato)(trans-1-1,2-diaminocyclohexane)platinum(II) ($C_{12}H_{23}N_3O_5Pt$).

Melting point: 210°–214° C. (decomposition) Elemental analysis data: calcd. (%): C, 29.75; 4.79; N, 8.67 found (%): C, 29.65; H, 4.87; N, 8.83 $^{195}$Pt NMR (DMF-$d_7$) δ: −1655 $^1$H NMR (DMF-$d_7$) δ: 1.19 (2H, m), 1.46–1.67 (12H, m), 2.12 (2H, m), 2.60 (1H, m), 2.68 (2H, m), 5.82 (1H, br m), 5.94 (1H, br m), 6.83 (1H, br m), 6.95 (1H, br m)

EXAMPLE 8

(Compound 8)

The procedure of Example 1 was repeated except that 2.70 g (30 mmol) of l-lactic acid was used instead of acetic acid and the amount of the 1 N aqueous solution of sodium hydroxide was changed to 8 ml, thereby obtaining 2.76 g (40.0%) of crystals of 1-lactato(nitrato)(trans-1-1,2diaminocyclohexane)platinum(II) ($C_9H_{19}N_3O_6Pt$).

Melting point: 203°–207° C. (decomposition) Elemental analysis data: calcd. (%): C, 23.48; H, 4.16; N, 9.13 found (%): C, 23.49; H, 4.01; N, 8.70 $^{195}$Pt NMR (DMF-$d_7$) δ: −1658 $^1$H NMR (DMF-$d_7$) δ: 1.14 (3H, d, $J_{H-H}$=7.2 Hz), 1.20 (2H, m), 1.56 (4H, m), 2.14 (2H, m), 2.75 (2H, m), 4.20 (1H, q, $J_{H-H}$=7.2 Hz), 5.36 (1H, br), 5.86 (1H, br m), 6.21 (1H, br m), 6.97 (1H, br m)

EXAMPLE 9

(Compound 9)

The procedure of Example 1 was repeated except that 2.84 g (30 mmol) of chloroacetic acid was used instead of acetic acid and the amount of the 1 N aqueous solution of sodium hydroxide was changed to 9 ml, thereby obtaining 3.83 g (54.9%) of crystals of chloroacetato(nitrato)(trans-1-1,2-diaminocyclohexane)platinum(II) ($C_8H_{16}N_3O_5Pt$).

Melting point: 173°–178° C. (decomposition) Elemental analysis data: calcd. (%): C, 20.67; H, 3.47; N, 9.04 found (%): C, 20.57; H, 3.52; N, 9.11 $^1$H NMR (DMF-$d_7$) δ: 1.17 (2H, m), 1.55 (4H, m), 2.10 (2H, m), 2.52 (2H, m), 4.07 (2H, s), 5.40 (1H, br m), 5.50 (1H, br m), 6.40 (2H, br m)

EXAMPLE 10

(Compound 10)

A 2.00 g (4.56 mmol) portion of Compound 1 was suspended in 12 ml of formamide to which was subsequently added 800 mg of potassium chloride, followed by 90 minutes of stirring at room temperature. After completion of the reaction, the thus precipitated crystals were collected by filtration, washed with formamide and acetone in that order and then dried to obtain 1.12 g (60.8%) of crystals of acetato(chloro)(trans-1-1,2-diaminocyclohexane)platinum(II) ($C_8H_{17}ClN_2O_2Pt$).

Melting point: 230°–235° C. (decomposition) Elemental analysis data: calcd. (%): C, 23.80; H, 4.24; N, 6.94 found (%): C, 24.15; H, 4.05; N, 6.70 $^{195}$Pt NMR (DMSO-$d_6$) δ: −2009 $^1$H NMR (DMSO-$d_6$) δ: 0.98 (2H, m), 1.25 (2H, m), 1.42 (2H, m), 1.75 (3H, s), 1.85 (2H, m), 2.25 (2H, m), 5.07 (2H, br m), 5.47 (1H, br m), 6.08 (2H, br m)

EXAMPLE 11

(Compound 11)

The procedure of Example 10 was repeated except that a 2.00 g (4.56 mmol) portion of Compound 2 was used instead of Compound 1, thereby obtaining 1.25 g (68.0%) of crystals of acetato(chloro)(trans-dl-1,2-diaminocyclohexane)platinum(II) ($C_8H_{17}ClN_2O_2Pt$).

Melting point: 230°–235° C. (decomposition) Elemental analysis data: calcd. (%): C, 23.80; H, 4.24; N, 6.94 found (%): C, 23.92; H, 4.10; N, 6.77 $^{195}$Pt NMR (DMSO-d$_6$) δ: –2009 $^1$H NMR (DMSO-d$_6$) δ: 0.98 (2H, m), 1.25 (2H, m), 1.42 (2H, m), 1.75 (3H, s), 1.85 (2H, m), 2.25 (2H, m), 5.07 (2H, br m), 5.47 (1H, br m), 6.08 (1H, br m)

EXAMPLE 12

(Compound 12)

The procedure of Example 10 was repeated except that 2.00 g (4.48 mmol) of Compound 3 was used instead of Compound 1, thereby obtaining 0.90 g (45.3%) of crystals of chloro(glycolato)(trans-l-1,2-diaminocyclohexane)platinum(II) ($C_8H_{17}ClN_2O_3Pt \cdot \frac{1}{2}HCONH_2$).

Melting point: 220°–228° C. (decomposition) Elemental analysis data: calcd. (%): C, 21.72; H, 3.87; N, 6.33 found (%): C, 21.64; H, 3.83; N, 6.35 $^{195}$Pt NMR (DMSO-d$_6$) δ: –2001 $^1$H NMR (DMSO-d$_6$) δ: 0.97 (2H, m), 1.22 (2H, m), 1.43 (2H, m), 1.86 (2H, m), 2.10 (2H, m), 3.73 (2H, d, $J_{H-H}$=5.4 Hz), 3.84 (1H, t, $J_{H-H}$=5.4 Hz), 5.08 (2H, br m), 5.56 (1H, br m), 6.01 (1H, br m)

EXAMPLE 13

(Compound 13)

The procedure of Example 10 was repeated except that 2.00 g (4.48 mmol) of Compound 4 was used instead of Compound 1, thereby obtaining 0.95 g (48.0%) of crystals of chloro(glycolato)(trans-dl-1,2-diaminocyclohexane)platinum(II) ($C_8H_{17}ClN_2O_3Pt \cdot \frac{1}{2}HCONH_2$).

Melting point: 220°–228° C. (decomposition) Elemental analysis data: calcd. (%): C, 21.72; H, 3.87; N, 6.33 found (%): C, 21.90; H, 3.97; N, 6.29 $^{195}$Pt NMR (DMSO-d$_6$) δ: –2001 $^1$H NMR (DMSO-d$_6$) δ: 0.97 (2H, m), 1.22 (2H, m), 1.43 (2H, m), 1.86 (2H, m), 2.10 (2H, m), 3.73 (2H, d, $J_{H-H}$=5.4 Hz), 3.84 (1H, t, $J_{H-H}$=5.4 Hz), 5.08 (2H, br m), 5.56 (1H, br m), 6.01 (1H, br m)

EXAMPLE 14

(Compound 14)

The procedure of Example 10 was repeated except that 2.00 g (4.50 mmol) of Compound 5 was used instead of Compound 1, thereby obtaining 1.53 g (73.5%) of crystals of chloro(propionato)(trans-l-1,2-diaminocyclohexane)platinum(II) ($C_9H_{19}ClN_2O_2Pt \cdot HCONH_2$).

Melting point: 220°–224° C. (decomposition) Elemental analysis data: calcd. (%): C, 25.95; H, 4.79; N, 9.08 found (%): C, 25.91; H, 4.87; N, 9.02 $^{195}$Pt NMR (DMF-d$_6$) δ: –2009 $^1$H NMR (DMSO-d$_6$) δ: 0.91 (3H, t, $J_{H-H}$=7.2 Hz), 0.96 (2H, m), 1.25 (2H, m), 1.42 (2H, m), 1.86 (2H, m), 2.03 (2H, q, $J_{H-H}$=7.2 Hz), 2.15 (2H, m), 5.03 (2H, br m), 5.47 (1H, br m), 6.12 (1H, br m)

EXAMPLE 15

(Compound 15)

The procedure of Example 10 was repeated except that 2.00 g (4.39 mmol) of Compound 6 was used instead of Compound 1, thereby obtaining 1.28 g (61.4%) of crystals of chloro (cyclopropanecarboxylato) (trans-l-1,2-diaminocyclohexane)platinum(II) ($C_{10}H_{19}ClN_2O_2Pt \cdot HCONH_2$).

Melting point: 220°–225° C. (decomposition) Elemental analysis data: calcd. (%): C, 27.82; H, 4.67; N, 8.85 found (%): C, 27.72; H, 4.52; N, 8.50 $^{195}$Pt NMR (DMF-dT) δ: –1989 $^1$H NMR (DMSO-d$_6$) δ: 0.56 (4H, m), 1.14 (2H, m), 1.40 (1H, m), 1.50 (4H, m), 2.01 (2H, m), 2.79 (2H, m), 5.21 (2H, br m), 5.62 (1H, br m) I 6.38 (1H, br m)

EXAMPLE 16

(Compound 16)

The procedure of Example 10 was repeated except that 2.00 g (4.13 mmol) of Compound 7 was used instead of Compound 1, thereby obtaining 1.41 g (67.7%) of crystals of chloro(cyclopentanecarboxylato)(trans-1-1,2-diaminocyclohexane)platinum(II) ($C_{12}H_{23}ClN_2O_2Pt \cdot HCONH_2$).

Melting point: 225°–228° C. (decomposition) Elemental analysis data: calcd. (%): C, 31.04; H, 5.21; N, 8.36 found (%): C, 31.22; H, 5.49; N, 8.32 $^1$H NMR (DMSO-d$_6$) δ: 0.97 (2H, m), 1.24–1.90 (12H, m), 2.13 (2H, m), 2.48 (1H, m), 2.51 (2H, m), 5.04 br m), 5.47 (1H, br m), 6.18 (1H, br m)

EXAMPLE 17

(Compound 17)

The procedure of Example 10 was repeated except that 2.00 g (4.35 mmol) of Compound 8 was used instead of Compound 1, thereby obtaining 1.25 g (66.3%) of crystals of chloro(1-lactato)(trans-1-1,2-diaminocyclohexane)platinum(II) ($C_9H_{19}ClN_2O_3Pt$).

Melting point: 212°–215° C. (decomposition) Elemental analysis data: calcd. (%): C, 24.92; H, 4.41; N, 6.46 found (%): C, 24.83; H, 4.58; N, 6.36 $^{195}$Pt NMR (DMF-d$_7$) δ: –1997 $^1$H NMR (DMSO-d$_6$) δ: 1.14 (2H, m), 1.17 (3H, d, J=7.2 Hz), 1.51 (4H, m), 2.05 (2H, m), 2.75 (2H, m), 3.91 (1H, q, J=7.2 Hz), 4.05 (1H, br), 5.30 (2H, br m), 5.75 (1H, br m), 6.33 (1H, br m)

TEST EXAMPLE 1

Antitumor effect on murine L1210 leukemia cell:

Murine L1210 leukemia cells (1×10$^5$ cells) were inoculated peritoneally into six-week-old male CDF$_1$ mice. The mice were observed for 30 days and a percent increase in life-span (ILS) was calculated by the following equation based on mean survival days of a drug-treated group and an untreated group.

$$ILS(\%) = (T/C - 1) \times 100$$

T: mean survival days of drug-treated group
C: mean survival days of untreated group Also, an ILS$_{50}$ value (a dose which shows 50% of the ILS value by 5 administrations) was calculated from a linear regression line based on the ILS values of respective doses of each sample, and a therapeutic index TI (LD$_{50}$/ILS$_{50}$) was calculated from an LD$_{50}$ value (50% lethal dose by single intraperitoneal administration). The results are shown in Table 1. In the table, ILS$_{max}$ means the maximum ILS value (%) within the set doses, and its corresponding dose (mg/kg) is shown in parenthesis.

TABLE 1

| Compound tested | ILS$_{max}$ (%) | (mg/kg) | LD$_{50}$ (mg/kg) | ILS$_{50}$ (mg/kg) | TI |
|---|---|---|---|---|---|
| Cisplatin | 97.5 | (4) | 18.0 | 1.3 | 13.8 |
| Compound 14 | 146.3 | (8) | 44.3 | 1.0 | 44.3 |
| Compound 15 | >166.3 | (8) | 31.3 | 1.2 | 26.1 |
| Compound 16 | >221.3 | (32) | 176.8 | 5.6 | 31.6 |
| Compound 17 | >190.0 | (8) | 44.3 | <1.0 | >44.3 |

TEST EXAMPLE 2

Antitumor effect on cisplatin-resistant murine L1210 leukemia cell:

The above test of the antitumor effect on murine leukemia cells was repeated except that cisplatin-resistant murine L1210 leukemia cell (L1210/DDP) was used instead of murine L1210 leukemia cell, with the results shown in Table 2.

TABLE 2

| Compound tested | ILS$_{max}$ (%) | (mg/kg) | LD$_{50}$ (mg/kg) | ILS$_{50}$ (mg/kg) | TI |
|---|---|---|---|---|---|
| Cisplatin | 1.0 | (4) | 18.0 | ND | ND |
| Compound 14 | >194.1 | (1,2,4) | 44.3 | <1.0 | >44.3 |
| Compound 15 | >194.1 | (1,2) | 31.3 | <1.0 | >31.3 |
| Compound 16 | >194.1 | (4,8) | 176.8 | <4.0 | >44.2 |
| Compound 17 | >194.1 | (1,2) | 44.3 | <1.0 | >44.3 |

ND: not detectable

As is evident from the results shown in Tables 1 and 2, the platinum complex (1) of the present invention is a compound which has excellent antitumor effects and high safety. Also, each of the platinum complexes (1) of the present invention was found to be highly soluble in water.

Thus, it is apparent that the platinum complex of the present invention has excellent antitumor effects and high safety and is highly soluble in water, so that it is useful as an agent for use in the treatment of various malignant tumors.

While the invention has been described in detail and with reference to specific embodiments thereof, it will be apparent to one skilled in the art that various changes and modifications can be made therein without departing from the spirit and scope thereof.

What is claimed is:

1. A platinum complex represented by the following formula (1):

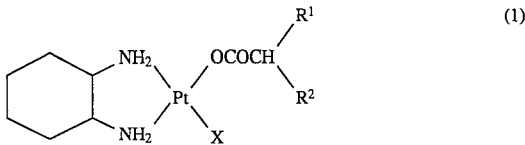

wherein X represents a halogen atom or a nitrate ion; and $R^1$ and $R^2$ may be the same or different from each other and each represents a hydrogen atom, a halogen atom, a hydroxyl group or an alkyl group, or both form a cycloalkyl group together with the adjacent carbon atom.

2. The platinum complex of claim 1, wherein said alkyl group represented by $R^1$ and $R^2$ is a straight-chain or branched alkyl group having 1 to 9 carbon atoms.

3. The platinum complex of claim 1, wherein said alkyl group represented by $R^1$ and $R^2$ is a straight-chain or branched alkyl group having 1 to 6 carbon atoms.

4. The platinum complex of claim 1, wherein said halogen atom represented by $R^1$ and $R^2$ is fluorine, chlorine, bromine or iodine.

5. The platinum complex of claim 1, wherein said cycloalkyl group formed by $R^1$ and $R^2$ together with the adjacent carbon atom is a 3- to 7-membered cycloalkyl group.

6. The platinum complex of claim 1, wherein said halogen atom represented by X is fluorine, chlorine, bromine or iodine.

7. A pharmaceutical composition comprising the platinum complex of claim 1 and a pharmaceutically acceptable carrier.

* * * * *